(12) United States Patent
Jarecki et al.

(10) Patent No.: US 11,642,314 B2
(45) Date of Patent: May 9, 2023

(54) MIXTURES OF BRANCHED CHAIN KETO ACIDS (BCKA) AND METHOD FOR THE PRODUCTION OF SUCH MIXTURES

(71) Applicant: Evonik Operations GmbH, Essen (DE)

(72) Inventors: Christine Jarecki, Middlesbrough (GB); Dieter Feit, Rodenbach (DE)

(73) Assignee: Evonik Operations GmbH, Essen (DE)

( * ) Notice: Subject to any disclaimer, the term of this patent is extended or adjusted under 35 U.S.C. 154(b) by 179 days.

(21) Appl. No.: 17/257,769

(22) PCT Filed: Jul. 26, 2019

(86) PCT No.: PCT/EP2019/070223
§ 371 (c)(1),
(2) Date: Jan. 4, 2021

(87) PCT Pub. No.: WO2020/025489
PCT Pub. Date: Feb. 6, 2020

(65) Prior Publication Data
US 2021/0290544 A1    Sep. 23, 2021

(30) Foreign Application Priority Data
Jul. 31, 2018    (EP) .................... 18186513

(51) Int. Cl.
*A61K 9/16*    (2006.01)
*A23L 33/175*    (2016.01)
*A61K 31/19*    (2006.01)
*A61K 33/06*    (2006.01)

(52) U.S. Cl.
CPC .......... *A61K 9/1682* (2013.01); *A23L 33/175* (2016.08); *A61K 31/19* (2013.01); *A61K 33/06* (2013.01)

(58) Field of Classification Search
CPC .................................................. A23L 33/175
See application file for complete search history.

(56) References Cited

U.S. PATENT DOCUMENTS

| 6,100,287 | A | 8/2000 | Stevens et al. |
| 2005/0239888 | A1 | 10/2005 | Franzone et al. |
| 2010/0280123 | A1 | 11/2010 | Karau et al. |
| 2015/0174088 | A1* | 6/2015 | Karau .................. A61K 31/194 |

FOREIGN PATENT DOCUMENTS

| WO | WO 99/25331 A1 | 5/1999 |
| WO | WO 2004/012706 A1 | 2/2004 |

OTHER PUBLICATIONS

Andreas Picker et al., The multiple effects of amino acids on the early stages of calcium carbonate crystallization, Z. Kristallogr. 2012, 227, 744-757, DOI 10.1524/zkri.2012.1569 (Year: 2012).*
Lara Štajneretal, The effect of different amino acids on spontaneous precipitation of calcium carbonate polymorphs, Journal of Crystal Growth, 486 (2018) 71-81 (Year: 2018).*
International Search Report and Written Opinion dated Oct. 2, 2019 in PCT/EP2019/070223 filed on Jul. 26, 2019.
Chinese Office Action dated Dec. 14, 2022, in Chinese Patent Application No. 201980050006.0 (with English Translation).

* cited by examiner

*Primary Examiner* — Mark V Stevens
*Assistant Examiner* — Alparslan Asan
(74) *Attorney, Agent, or Firm* — Oblon, McClelland, Maier & Neustadt, L.L.P.

(57) ABSTRACT

The present invention relates to a process for the production of a homogenous mixture of two or more branched chain keto acids wherein in a first step, two or more free keto acids are mixed, and in a second step, the mixed keto acids are co-crystallized with one or more alkaline earth metal salts, and foodstuff, food supplement or pharmaceutical products containing a mixture of branched-chain keto acids for supporting muscle structure, increasing muscle performance and improving general wellbeing with simultaneous relief of nitrogen detoxification metabolism by reduced nitrogen supply compared to the intake of the corresponding amino acids and an improved nitrogen metabolism in the body.

17 Claims, 8 Drawing Sheets

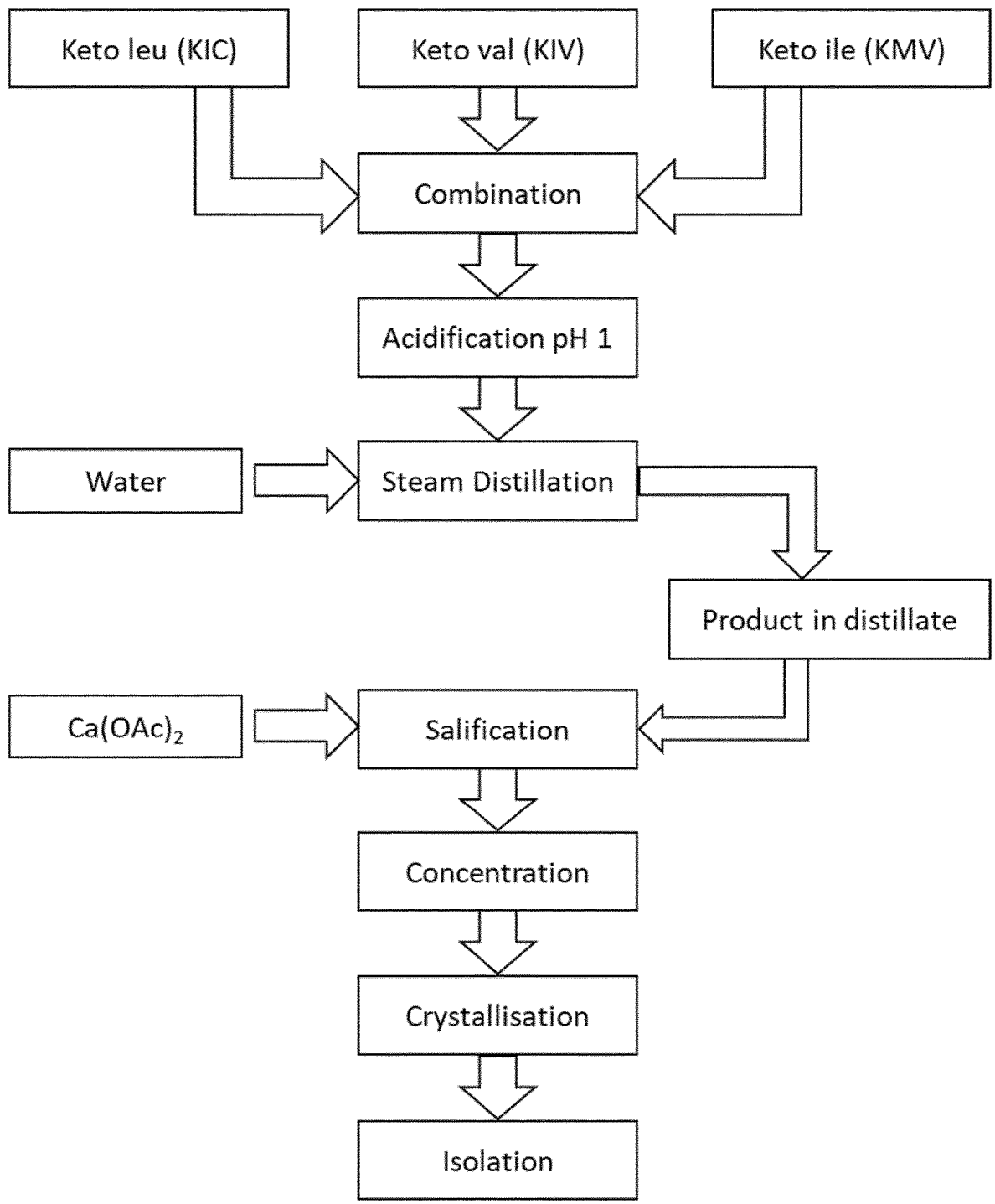
Fig. 1: Co-distillation and co-crystallisation of approximate 2:1:1 keto leucine : keto valine : keto isoleucine calcium salts Fig. 2: Area % composition of free keto acids during combined steam distillation
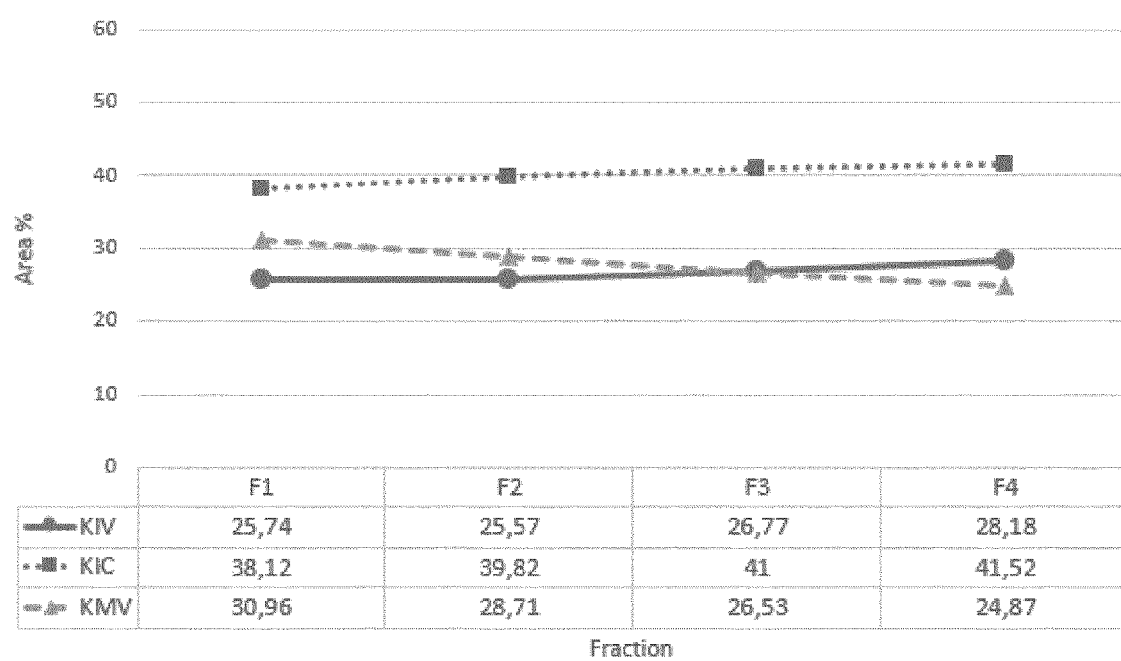

Fig. 3: Microscope pictures of individual branched chain keto acid calcium salts, (magnitude: 100x, scale bar is 200 µm); a) Keto valine Ca salt; b) Keto leucine Ca salt; c) Keto isoleucine Ca salt
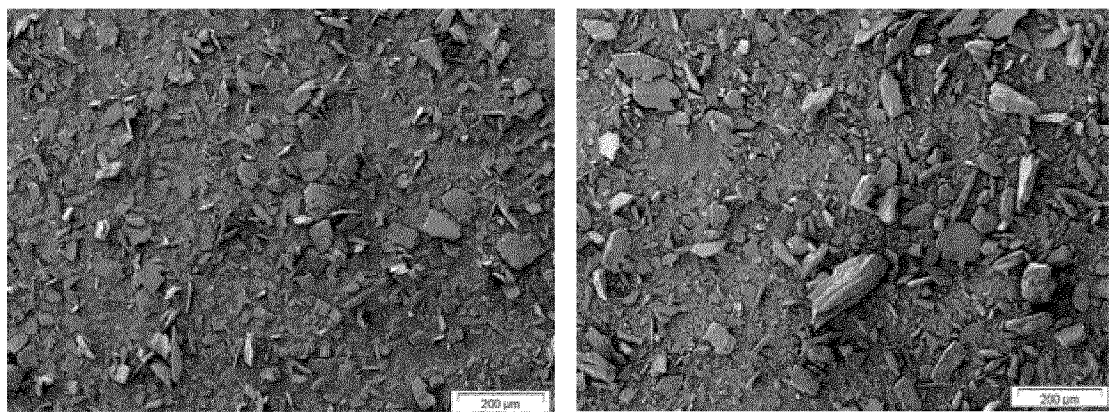
a)            b)
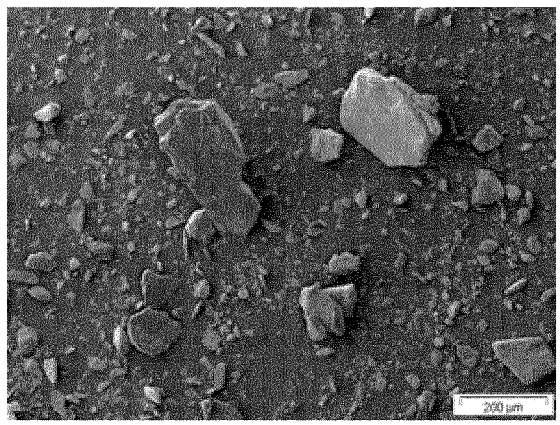
c)

Fig. 4: Particle size distribution (PSD) of individual branched chain keto acid calcium salts; a) Keto valine Ca salt; b) Keto leucine Ca salt; c) Keto isoleucine Ca salt – x axis showing particle size in μm and y axis showing % of particles. Red line depicts sum of particles.
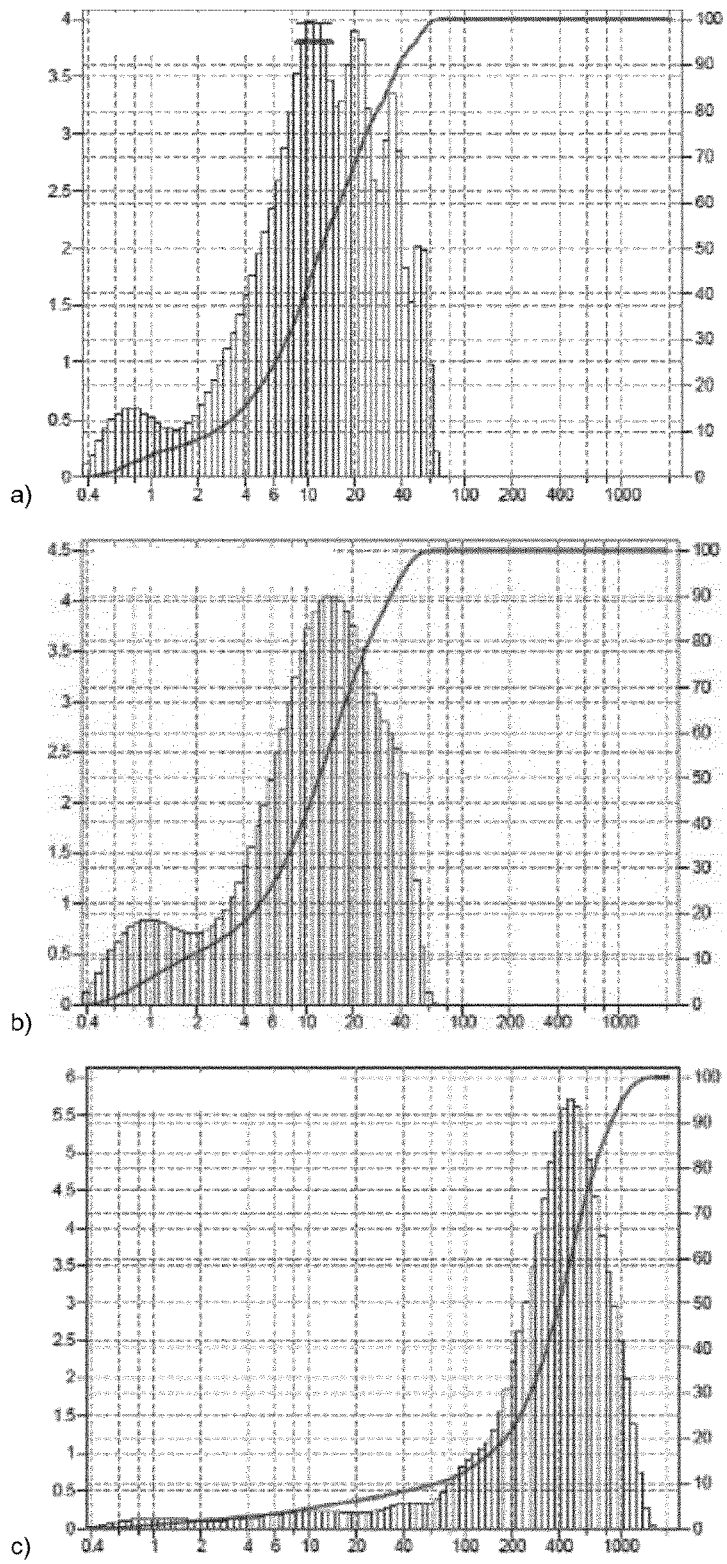

Fig. 5: Effect of mother liquor recycling on product composition
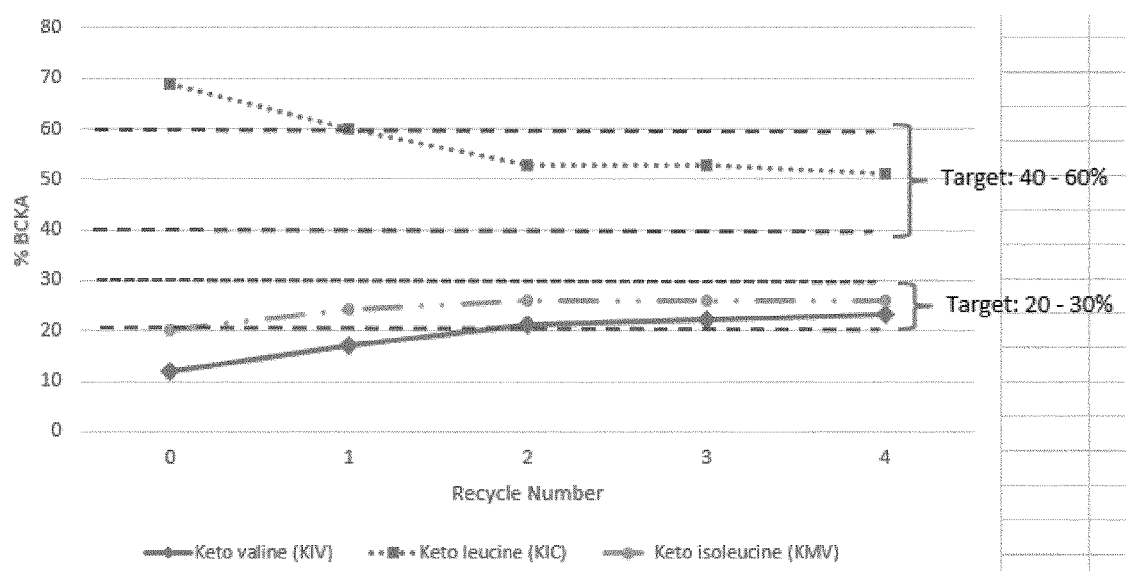

Fig. 6: Microscope picture of co-crystallized branched chain keto acid calcium salts (2:1:1 keto leucine : keto isoleucine : keto valine) (magnitude: 100x, scale bar is 200 μm)
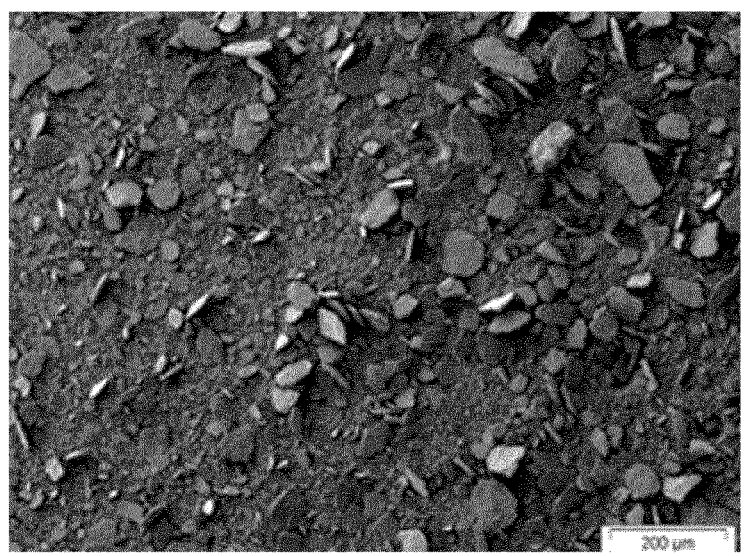

Fig. 7: Particle size distribution (PSD) of co-crystallized branched chain keto acid calcium salt (2:1:1 keto leucine : keto isoleucine : keto valine) - x axis showing particle size in μm and y axis showing % of particles. Red line depicts sum of particles.
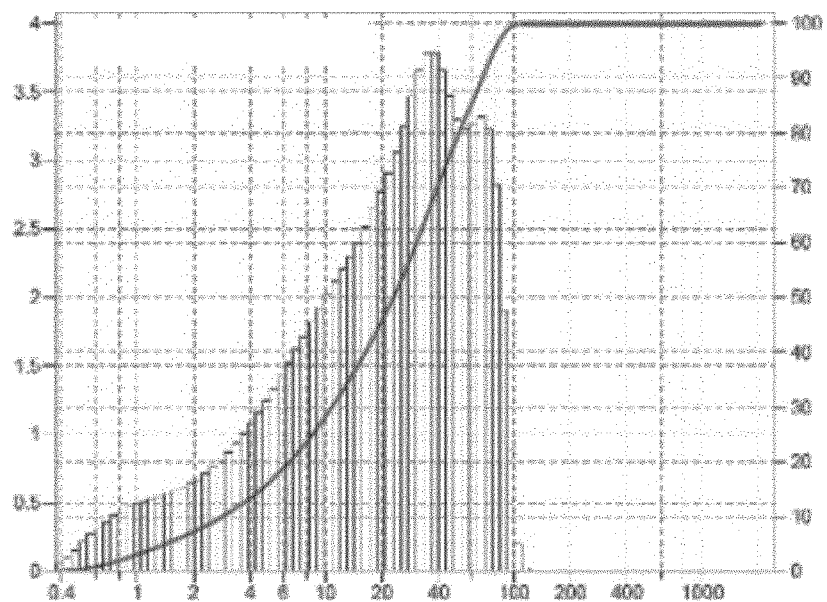

Fig. 8: Particle size distribution (PSD) of a) co-crystallized branched chain keto acid calcium salts (2:1:1 keto leucine : keto isoleucine : keto valine) and b) mixture of branched chain keto acid calcium salts (2:1:1 keto leucine : keto isoleucine : keto valine), x axis showing particle size in μm and y axis showing volume % of particles.
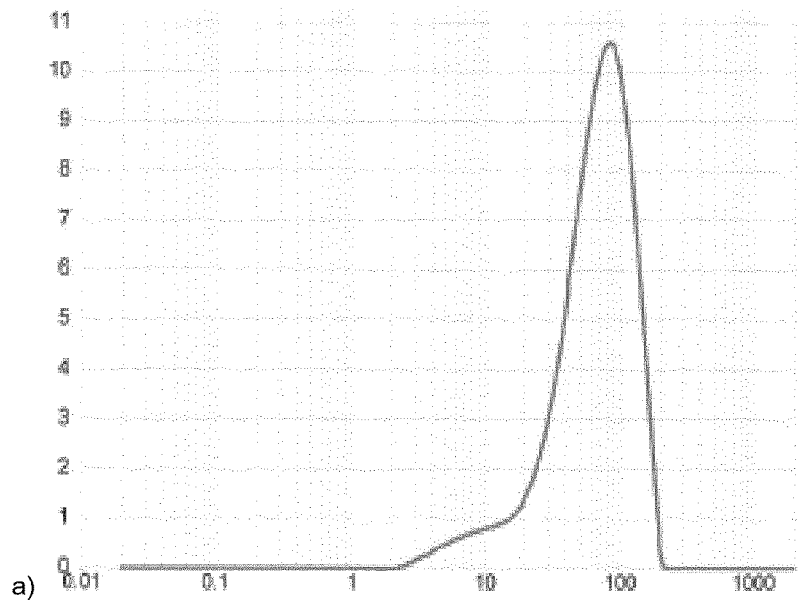
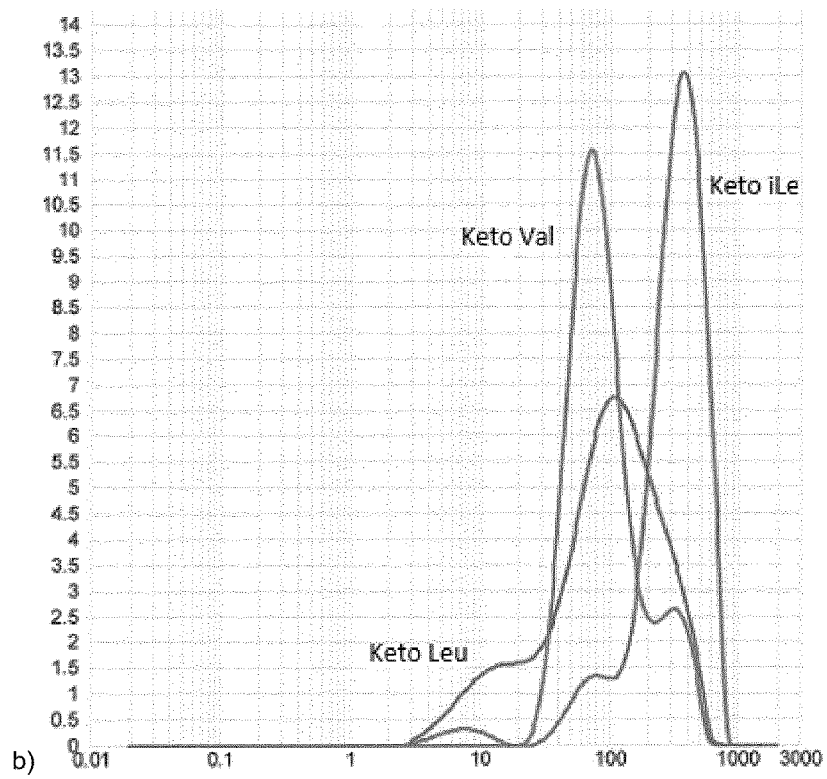

ns, proteins
MIXTURES OF BRANCHED CHAIN KETO ACIDS (BCKA) AND METHOD FOR THE PRODUCTION OF SUCH MIXTURES The present invention relates to a process for the production of a homogenous mixture of two or more branched chain keto acids wherein in a first step, two or more free keto acids are mixed, and in a second step, the mixed keto acids are co-crystallized with one or more alkaline earth metal salts. The invention is also related to foodstuff, food supplement and pharmaceutical products containing a mixture of branched-chain keto acids for supporting muscle structure, increasing muscle performance and improving general wellbeing with simultaneous relief of nitrogen detoxification metabolism by reduced nitrogen supply compared to the intake of the corresponding amino acids and an improved nitrogen metabolism in the body.

BACKGROUND

Lack of physical movement is a risk factor which can lead to decreased physical efficiency and thus to a reduced quality of life. In order to prevent the drop in physical efficiency, and to build it up again, physical training is essential, wherein a series of cellular processes such as, for example, muscle damage and muscle breakdown, muscle regeneration, muscle hypertrophy and muscle fiber transformation proceed. In the cellular processes, energy and protein metabolism plays a decisive role. Consequently, the supply of amino acids plays a decisive role with respect to the metabolic processes proceeding in muscle tissue. In particular, the branched-chain amino acids valine, leucine and isoleucine are essential substrates and important regulators in protein biosynthesis and a main source of nitrogen for glutamine and alanine synthesis in skeletal muscle. Alanine, in addition, is an important precursor for gluconeogenesis and glutamine acts as a nitrogen transporter between organs.

The average requirement for protein is approximately 660 mg/kg of body weight which, however, can be significantly increased by physical training. The requirement for protein can generally be covered by a balanced diet, which, however, is not readily achievable. Physical training, owing to an increased protein degradation and decreased protein synthesis, leads to an altered requirement for nutrients, in addition, a modified metabolic position results which, for example, is due to the effect of physical training on the hormone system and finally, there is also a lack of knowledge about a suitable diet with increasing physical load, especially in relation to age, so that malnutrition can occur rapidly.

For these reasons, the use of a food supplement appears logical in individuals which are subject to physical load. In this context, studies have already been carried out with differing results which related to the effect of a creatine supplementation on the efficiency of the subject. In addition, it is known that muscle regeneration can be promoted by a high carbohydrate supply.

The use of branched-chain amino acids (BCAA) as a dietetic substitute was studied likewise intensively in the past, but not with clear results. While in one study an increase in mental and physical performance by BCAA supplementation is reported (Blomstrand, E. et al., Eur. J. Appl. Physiol. Occup Physiol 63: 83-88, 1991), in another study, no effect on physical efficiency was found (van HG, Raaymakers, Saris, Wagenmakers, J. Physiol 486 (Pt3), 789-794, 1995).

Alpha-keto acids of branched-chain amino acids likewise play an important role in amino acid metabolism, especially in the skeletal muscle and liver. One-third of muscle protein consists of the branched-chain amino acids which cannot be formed by the body, but must be taken in with food. In the muscle, especially in the case of physical exertion, proteins are continuously synthesized and broken down, wherein in the breakdown of amino acids the corresponding alpha-keto acid is formed with transfer of the amino group to a carrier. The keto acid obtained can then be further oxidized enzymatically for energy production. The carrier is transported to the liver and there releases toxic ammonia, which must be converted to urea and excreted via the kidneys.

The use of alpha-keto acids which are derived from branched-chain amino acids for pharmaceutical purposes has long been known. For instance, alpha-keto isocaproate (keto leucine), in particular, can be used for reducing the protein breakdown in muscle and for a reduction of the formation of urea resulting from protein breakdown after muscle operations (U.S. Pat. No. 4,677,121). The use of keto leucine in malnutrition, muscular dystrophy or uremia and in other disorders which are a secondary consequence of protein breakdown in muscle is also described there. Keto leucine is administered in this case intravenously. In addition, it has been proposed to administer the alpha-keto acids of leucine, isoleucine and valine to patients who must maintain a protein-reduced diet, for example because of renal failure (U.S. Pat. No. 4,100,161). The role of alpha-keto acids within protein metabolism with respect to various medical indications is also described in Walser, M. et al., Kidney International, Vol. 38 (1990), pp. 595-604.

In the functional food sector, in contrast, the branched-chain amino acids are used directly for supporting muscle build-up, for example in athletes (Shimomura, Y. et al., American Society for Nutrition). The use of alpha-keto acids of leucine, isoleucine and valine for improving muscle performance and also for supporting muscle recovery after fatigue is described in U.S. Pat. No. 6,100,287, wherein salts of the corresponding anionic keto acids with cationic amino acids as counterion, such as, for example, arginine or lysine, are used. As a result, however, polyamines are also formed of which it is known that they can lead to apoptosis (programmed cell death). The excretion of the breakdown products of polyamines proceeds via the kidneys which are further stressed as a result.

WO 2008/122613 describes a food supplement containing alpha-keto analogues of branched-chain amino acids for supporting muscle structure, increasing muscle performance and improving general wellbeing with simultaneous relief of nitrogen detoxification metabolism by reduced nitrogen supply compared to the intake of the corresponding amino acids and an improved nitrogen metabolism in the body. Especially, food supplements which have a combination of alpha-keto isocaproate and alpha-keto isovalerate or alpha-keto beta-methylvalerate or a combination of alpha-keto isovalerate and alpha-keto beta-methylvalerate or a combination of all three alpha-keto acids or salts thereof are disclosed. Further, specific ratios for the different alpha-keto analogues are preferred.

It is known from US 2011/0257236A1 and U.S. Pat. No. 4,677,121 that both combinations of branched chain amino acids L-leucine, L-isoleucine and L-valine and their respective keto acids in an approximate ratio of 2:1:1 can suppress damage to muscles during intensive exercise. Moreover, it is already well established that the keto acids leucine, isoleucine, valine, and hyroxymethionine are used in a pharmaceutical, which is used to maintain protein levels in the case of chronic kidney disease (described in U.S. Pat. Nos. 4,100,160 and 4,100,161). Whereas the process and advantages of combined processing of the branched chain L-amino acids is reported, thus far, the processing of individual branched keto acid and hydroxymethionine as calcium salts have been reported.

However, when branched chain keto acid salts are produced separately and mixed at a later stage, the branched chain keto acid salts have different particle size distributions and also differ in their crystal forms. In particular, the calcium salt of keto isoleucine has very large crystals. As a consequence, it is difficult to prepare a homogenous mixture of the branched chain keto acid salts and the products must be milled to provide a homogenous mixture suitable for use in nutraceutical products. In order to provide homogenous mixtures with uniform particle size distribution, a dry blending process can be applied for example, where several components with varying particle size need to be weighted, premixed, milled and mixed again to ensure homogeneity. According to the desired composition in the mixture, as a first step, appropriate amounts of individual released amino acids are weighted for premixing step. For premixing the mixture needs to be transferred and mixed in a dryer, in order to obtain a homogenous mixture. In the next step, the mixture needs to be milled to obtain an appropriate uniform particle size distribution. In a final mixing step, the mixture needs to be transferred in a dryer in order to obtain a homogenous amino acid mixture.

Proceeding from the prior art, there is a need for food supplements with combinations of branched chain keto acids which promote wellbeing after sporting activities, increase muscle synthesis and efficiency of the muscle and permanently lower the nitrogen burden of metabolism. More specifically, there is the need for homogenous mixtures consisting of branched chain keto acids in predefined ratios and for simplified processes for the production of homogenous mixtures with a uniform particle distribution containing keto and hydroxyl components of keto analogues and essential amino acids.

SUMMARY

The problem is solved by providing a process for the production of a homogenous mixture of two or more keto acids wherein
in a first step, two or more branched chain keto acids are mixed, and
in a second step, the mixed keto acids are co-crystallized with one or more alkaline earth metal salts.

BRIEF DESCRIPTION OF DRAWINGS

FIG. 1 illustrates a process flow showing co-distillation and co-crystallisation of approximate 2:1:1 keto leucine: keto valine:keto isoleucine calcium salts.

FIG. 2 shows area % composition of free keto acids during combined steam distillation.

FIG. 3 shows microscope pictures of individual branched chain keto acid calcium salts, (magnitude: 100x, scale bar is 200 μm); a) Keto valine Ca salt; b) Keto leucine Ca salt; c) Keto isoleucine Ca salt.

FIG. 4 shows particle size distribution (PSD) for calcium salts of keto valine, keto leucine and keto isoleucine; a) Keto valine Ca salt; b) Keto leucine Ca salt; c) Keto isoleucine Ca salt–x axis showing particle size in pm and y axis showing % of particles. The line depicts sum of particles.

FIG. 5 shows effect of mother liquor recycling on product composition.

FIG. 6 shows a microscope picture of co-crystallized branched chain keto acid calcium salts (2:1:1 keto leucine: keto isoleucine:keto valine) (magnitude: 100x, scale bar is 200 μm).

FIG. 7 shows particle size distribution (PSD) of co-crystallized branched chain keto acid calcium salt (2:1:1 keto leucine:keto isoleucine:keto valine) - x axis showing particle size in μm and y axis showing % of particles. The line depicts sum of particles.

FIG. 8 shows particle size distribution (PSD) of a) co-crystallized branched chain keto acid calcium salts (2:1:1 keto leucine:keto isoleucine:keto valine); and b) mixture of branched chain keto acid calcium salts (2:1:1 keto leucine: keto isoleucine:keto valine), x axis showing particle size in μm and y axis showing volume % of particles.

DETAILED DESCRIPTION

It was a surprising finding that after co-crystallization of two or more keto acids no additional processing is necessary to achieve homogeneity with this product. The mixture obtained has a uniform particle size distribution and a homogenous crystal form.

In a preferred embodiment, the alkaline earth metal is chosen from magnesium and calcium, preferably calcium.

It is particularly preferred, when the alkaline earth metal salt is chosen from calcium carbonate, calcium hydroxide, calcium acetate, calcium chloride, calcium oxide, magnesium hydroxide and magnesium acetate.

The keto acids used in the process according to the present invention are chosen from keto leucine, keto valine, keto isoleucine, keto phenylalanine and hydroxymethionine in an alternative embodiment of the present invention. In a preferred embodiment the keto acids are chosen from keto leucine, keto valine and keto isoleucine.

In one embodiment of the present invention, the free keto acids are charged in the desired molar ratio to water or a mother liquor solution, into which a stoichiometric amount of alkaline earth metal salt has been charged.

In this embodiment, the aqueous phase is saturated with the product, preferably by recycling of the mother liquor. This recycling of the mother liquors has an unexpected effect—due to optimal saturation of the mother liquors, it was found that the target composition could be achieved without adjusting the composition to compensate for varying solubility. The free acids are charged in the desired ratio to a mother liquor solution into which a stoichiometric amount of calcium salt has been charged.

In an alternative embodiment, the free keto acid is added as aqueous solution or as a solution in an organic solvent, preferably chosen from methyl isobutyl ketone, acetone and tert-butyl methyl ether.

In a preferred configuration of the present invention, the mixed keto acids are purified before the co-crystallization step, using one of the following: steam distillation, solvent extraction, ion exchange chromatography or crude crystallization with an alkaline earth metal salt.

The keto acids can be produced via chemical synthesis or via fermentation processes. Purification is normally achieved by solvent extraction, or by steam distillation, followed by salification.

In a further preferred configuration of the present invention, the mixed keto acids are purified using combined steam distillation, affording an aqueous solution of purified keto acids in a ratio similar to the inputs. This was a surprising result given the differences in boiling point:keto valine free acid (70-80° C. at 5 mbar), keto leucine free acid (~100° C. at 5 mbar) and keto isoleucine free acid (~115° C. at 5 mbar).

A further subject of the present invention is a mixture of at least two keto acids obtainable by a process as described above, wherein the mixture contains mixed alkaline earth metal salts and has a uniform particle size distribution and a homogenous crystal form.

In a preferred embodiment of the present invention, the size of the particles in the mixture is not larger than 400 µm, preferably not larger than 300 µm, more preferably not larger than 200 µm or most preferably not larger than 150 µm.

In a particularly preferred configuration, the mixture contains mixed calcium or magnesium salts of keto leucine and keto isoleucine.

In a particularly preferred configuration, the mixture contains mixed calcium or magnesium salts of keto leucine and keto valine.

In a particularly preferred configuration, the mixture contains mixed calcium or magnesium salts of keto isoleucine and keto valine.

In a particularly preferred configuration, the mixture contains mixed calcium or magnesium salts of keto leucine, keto isoleucine and keto valine in an approximate ratio of 2:1:1.

In a particularly preferred configuration, the mixture contains mixed calcium or magnesium salts of keto leucine, keto isoleucine, keto valine, hydroxymethionine and keto phenylalanine.

The present invention is also directed to foodstuff, a food supplement or a pharmaceutical product containing a mixture of keto acids according to the embodiments described above.

In addition, further nitrogen-free additives can be added to the food supplement. Those which may be stressed in particular are energy-giving compounds, preferably from the group of carbohydrates, such as, for example, glucose, but also additives which promote the regeneration process, such as, for example, vitamins, in particular vitamin A, vitamin B1, B2, B6 and B12, vitamin C, vitamin D, vitamin E, vitamin K, pantothenic acid, niacin, folic acid, biotin, choline and inositol. In addition, antioxidants can be present in the food supplement such as, for example, beta-carotene, potassium citrate, citric acid, lactic acid, tocopherol, sodium ascorbate or potassium ascorbate or ascorbic acid. Minerals and trace elements from the group of sodium, potassium, magnesium, calcium, iron, zinc, manganese, copper, selenium, chromium, phosphorus and iodine are likewise possible as additives. The said additives in this case are added in the amounts conventional for the food sector.

Preferred food supplements can contain, for example (the quantities in each case are the preferred daily dose):
10-500 mg of sodium,
10-500 mg of potassium,
50-500 mg of calcium,
10-300 mg of magnesium,
1-20 mg of zinc,
5-50 mg of iron,
0.1-1 mg of iodine,
5-100 µg of selenium,
5-100 µg of chromium,
up to 100 mg of vitamin B1,
up to 100 mg of vitamin B2,
up to 100 mg of vitamin B6,
up to 200 mg of vitamin B12,
up to 5 g of vitamin C,
up to 500 mg of vitamin E,
up to 300 mg of pantothenic acid,
up to 1 g of niacin,
up to 10 mg of folic acid,
up to 1 mg of biotin.

Further additives which come into consideration as an addition are saturated or unsaturated fatty acids, in particular C6-C22 fatty acids. In addition, use can be made of fats and oils from the group sunflower, sesame, rapeseed, palm, castor oil, coconut, safflower, soybean, pork lard, beef tallow and fish oil. In addition, preservatives, food dyes, sweeteners, flavor enhancers and/or aroma substances can be present in the food supplement in the customary amounts known to those skilled in the art. In particular, as additives, taste-masking substances come into consideration since, for example, free alpha-keto acids can taste acidic or their salts can taste unpleasant. If the additives employed are used in relatively large amounts, recourse is made in this case to nitrogen-free additives. Particularly preferred food supplements, however, do not contain nitrogenous additives.

The claimed food supplements can be used, for example, in the form of a powder, a tablet, a minitablet, a pellet, a granule, a sachet, a capsule, or in the form of a solution or suspension. In tablet form, the alpha-keto acids or salts thereof are preferably formulated with approximately 30 to 80 percent by volume in the food supplement, preferably using nitrogen-free additives, in particular carbohydrates, fats and oils, and, if appropriate, also amino acids, such as, for example, leucine, isoleucine and valine, which can be present in the food supplement at approximately 70 to 20 percent by volume.

A capsule for instance may be filled with the inventive composition in the form of coated pellets or with coated granules, where "coated" means at least coated with coating layer. In another embodiment a capsule coated itself with a coating layer may filled with coated or uncoated pellets, with a powder or with coated or uncoated granules.

If direct administration of the food supplement in the form of a powder or a tablet is desired, the addition of conventional carriers can be advantageous. Suitable carriers are, for example, linear or (hyper)branched polyesters, polyethers, polyglycerols, polyglycolides, polylactides, polylactide-coglycolides, polytartrates and polysaccharides or polyethyleneoxide-based dendrimers, polyether dendrimers, coated PAMAM dendrimers, such as, for example, polylactide-coglycolide coating, or polyaryl ethers.

The tablet, pellet or capsule can in addition be provided with a coating, in order, for example, to permit the release of the food supplement first in the intestinal tract. The following encapsulating materials are preferably used in this case: carboxymethyl cellulose, nitrocellulose, polyvinyl alcohol, shellac, carrageenan, alginates, gelatin, cellulose acetate phthalate, polyvinyl acetate phthalate, hydroxypropyl methylcellulose phthalate, hydroxypropyl methylcellulose acetate succinate (HPMC-AS), cellulose acetate trimellitate, ethylcellulose, polyglycerols, polyesters or copolymers based on methacrylic acid and methacrylic/acrylic esters or their derivatives (such as Eudragit® for example).

If, in contrast, a solution or suspension of the food supplement is administered, the addition of emulsifiers or colloids can be useful, in order to be able to take up all desired components as well as possible in an aqueous system. Suitable additives are, for example, polyvinyl alcohols, glycerides of edible fatty acids, their esters of acetic acid, citric acid, lactic acid or tartaric acid, polyoxyethylene stearates, carbohydrate esters, propylene glycol esters, glycerol esters or sorbitan esters of edible fatty acids or sodium lauryl sulfate.

The present invention further relates to foods (functional foods) which contain the claimed food supplement. These can be, for example, drinks or bars which are particularly suitable for consuming the food supplement.

The foods in this case can be admixed with the claimed food supplement during their production, or a formulation of the food supplement can be added later to the food, for example in the form of a powder or a tablet. The dissolution of effervescent tablets or of a powder in mineral water can be mentioned here by way of example.

The use of the described food supplements or food can in principle be possible all day, but in particular during or after physical exertion is advisable. Physical training causes a muscular adaptation including muscle damage, muscle hypertrophy and muscle transformation. In this case, a training unit is considered a combination of a training phase and a regeneration phase. A suboptimal design of the training unit can lead, for example, to an overtraining syndrome which is expressed in a long-lasting tiredness with reduced physical efficiency. Such an overtraining syndrome is frequently caused or amplified by malnutrition.

In the said aspects, the food supplement of the invention is directed, in particular, to athletes, in this case both recreational and top athletes, including power athletes, and also those interested in health and fitness. The use of food supplements by older persons who, as is known, frequently have a restricted nitrogen economy and restricted nitrogen excretion capacity, is likewise particularly advantageous.

The present invention further relates to the use of the claimed food supplements for producing products which can be taken orally such as, for example, functional foods, in particular drinks, gels, creams, broths, energy bars, etc., and also tablets, powders which, for example, can be offered in sachets, bags, tubes, and for supporting muscle build-up, the efficiency of the musculature, for protection of the musculature against cell damage under stress, for increasing general wellbeing, general physical efficiency and for supporting muscle regeneration after physical stress with simultaneous relief of metabolism with respect to nitrogen detoxification.

The present invention also covers food for medical purpose, such as food, beverage, supplements, special food for medical purpose or pharmaceutical products.

Therefore, the invention also covers the use of a mixture according to the embodiments described above for the preparation of foodstuffs, food supplements or pharmaceutical products.

EXAMPLES

The starting materials of the process are aqueous sodium salt solutions of the keto acids prepared via chemical or fermentative processes. The preferred concentration of the starting solutions are listed in table 1.

TABLE 1 preferred concentration of starting solutions
of single keto acid sodium salts

| | Approximate concentration in % w/w (percentage by weight) | | |
|---|---|---|---|
| | Keto leucine (Na) | Keto isoleucine (Na) | Keto valine (Na) |
| Fermentation | 5 % w/w | up to 20 % w/w | 5 % w/w |
| Chemical process | up to 7 % w/w | up to 20 % w/w | up to 9 % w/w |

The keto acids may be produced via previously reported chemical or fermentation processes. Purification can be achieved by steam distillation, solvent extraction or crude precipitation from a fermentation solution, followed by salification.

An example for a process flow is depicted in FIG. 1 showing co-distillation and co-crystallisation of approximate 2:1:1 keto leucine:keto valine:keto isoleucine calcium salts. As shown in FIG. 1 the branched chain keto acids keto leucine (KIC) keto valine (KIV) and keto isoleucine (KMV) are combined and acidified at about pH 1. With addition of water a combined steam distillation is performed followed by a salification using $Ca(OAc)_2$. The resulting product is concentrated and co-crystallized and can be isolated in the last step.

Example 1: Purification of Branched Chain Keto Acids (BCKA) Using Combined Steam Distillation To an acid resistant vessel, the sodium salt solutions of keto leucine (331 g of 6.9% w/w solution, containing 22.8 g of sodium salt), keto isoleucine (61 g of 18.8% w/w solution, containing 11.4 g of sodium salt) and keto valine (144 g of 8.6% w/w solution, containing 12.4 g of sodium salt) were charged in the concentrations specified in the above to give a ratio on active basis of 2:1:1.2. The keto valine amount described in this example applies to the use of fresh liquors for salification (see examples 5-7 for description). When recycled mother liquors are used, the portion of keto valine can be reduced to 1.

At ambient temperature with stirring, 165 g 50% w/w sulphuric were charged to adjust the pH of the solution to pH<1. After pH adjustment, heat and vacuum were applied to achieve distillation at 60-80° C./200-300 mbar, (higher temperatures will lead to thermal decomposition of the free keto acids).

Further water was added and distilled at 80° C. maximum under 270-300 mbar vacuum until approximately 42 g/g keto acid has been distilled. The distillate contained 2.2 weight % of BCKA.

It was found that the three branched chain keto acids could be simultaneously distilled, affording an aqueous solution of purified keto acids in a ratio similar to the inputs (see FIG. 2, showing area % composition of free keto acids during combined steam distillation).

Analysis of the sump (residue) shows that the recovery of the keto acid is nearly quantitative. Moreover, it was found that combined distillation was more efficient overall with respect to steam consumption when compared with the distillation of the individual keto acids. This was particularly the case for keto isoleucine as shown in FIG. 2.

TABLE 2

Efficiency of free keto acid distillation
expressed in g/water per g of free acid

| | Total weight | Content keto acids | g water/ g keto acid |
|---|---|---|---|
| Keto acid mixture | 529.8 g | 12.0 g | 44.2 |
| Keto leucine | 534.0 g | 12.0 g | 44.5 |
| Keto valine | 425.6 g | 12.0 g | 35.5 |
| Keto isoleucine | 638.3 g | 12.0 g | 53.2 |

Example 2: Purification of Branched Chain Keto Acids Using Solvent Extraction

The following keto acids as their respective free acid, sodium salt or calcium salt forms are added to water to afford a ca. 5% w/v solution in the following molar ratio: keto valine:keto leucine:keto isoleucine 1:2:1. The solution is adjusted at ambient temperature to pH<1 with aqueous hydrochloric acid, then the acidic solution is extracted with methylisobutylketone (MIBK). The MIBK solution containing the free keto acids is heated to 60° C., then calcium carbonate solid is added to adjust the pH to >3 (target: 3-5, slightly exceeded in the given example). The biphasic mixture is heated to 80° C., the layers are allowed to settle then are separated. The lower aqueous (product containing) layer is further extracted with MIBK at 80° C. to remove impurities and following vacuum distillation to remove the remaining MIBK and to partly concentrate the batch, the aqueous layer is cooled to ambient temperature to crystallise the product. The solids are isolated by filtration, washed with water, then dried at maximum 75° C. under vacuum until dry.

Example 3: Purification of Branched Chain Keto Acids by Precipitation from a Fermentation Solution An approximately 5% aqueous solution of keto leucine fermentation solution is acidified with aqueous hydrochloric acid to pH 2. Calcium carbonate solid is charged at ambient temperature until the pH is >3 (target: ~3-5). The precipitated solids are isolated by filtration, washed with water, then dried at maximum 75° C. under vacuum until dry.

Example 4 (Comparative): Preparation of Calcium Salts of Individual Branched Chain Keto Acids The process for crystallisation of the free keto acids (or more precisely, salification) with calcium salts (typically calcium carbonate, calcium hydroxide or calcium acetate) is well established. The free keto acid may be added as aqueous solution if sufficiently diluted or as a solution in an organic solvent or solvents such as (but not limited to) methyl isobutyl ketone, acetone, tert-butylmethyl ether.

When the three keto acid salts are made separately, they have different particle size distributions, and are also quite different in their crystal forms. FIG. 3 shows microscope pictures of individual branched chain keto acid calcium salts, (magnitude: 100×, scale bar is 200 μm); a) Keto valine Ca salt; b) Keto leucine Ca salt; c) Keto isoleucine Ca salt. In particular, the calcium salt of keto isoleucine has particularly large crystals. The corresponding particle size distribution (PSD) of the individual branched chain keto acid calcium salts is shown in FIG. 4 and clearly shows the varying particle size distribution for the calcium salts of keto valine, keto leucine and keto isoleucine; a) Keto valine Ca salt; b) Keto leucine Ca salt; c) Keto isoleucine Ca salt x axis showing particle size in μm and y axis showing % of particles. Red line depicts sum of particles.

As a consequence, it is difficult to prepare a homogeneous mixture of the keto acid salts, and the products must be milled to give a mixture suitable for use in a nutraceutical product or any other application.

Example 5: Preparation of Mixture of Calcium Salts (with Calcium Acetate)

The composition of the starting free keto acids in the case of the co-crystallisation has to consider the variability in the solubility of the calcium salts (compare table 3, showing solubility in water in g/L at 20° C.) in order to achieve the desired ratio in the finished product:

TABLE 3

| Water solubility of keto acids and α-hydroxymethionine (in g/L at 20° C.) |||
| --- | --- | --- |
| Keto leucine | Keto isoleucine | Keto valine |
| 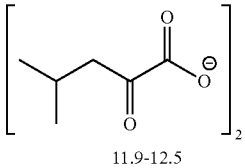 | 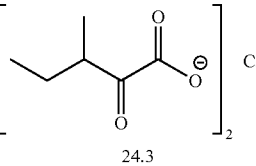 | 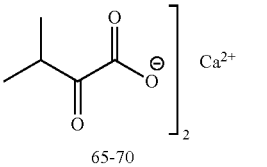 |
| 11.9-12.5 | 24.3 | 65-70 |
| Keto phenylalanine || α-hydroxymethionine |
| 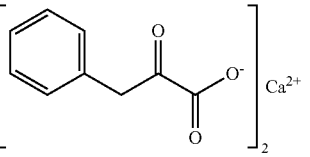 || 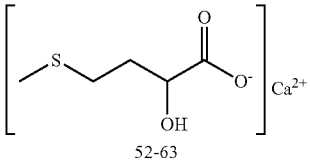 |
| 4.3-4.7 || 52-63 |

Generally, in order to maximise the yield of crystallisation processes, the recycling of mother liquors is frequently applied. In the case of the co-crystallisation, such recycling of the mother liquors had an unexpected effect due to optimal saturation of the mother liquors, it was found that the target composition could be achieved without adjusting the composition to compensate for varying solubility as described above it is possible to simply charge the free acids in the desired ratio to a mother liquor solution into which a stoichiometric amount of calcium salt has been charged. This is illustrated in FIG. 5 for the branched chain keto acids keto valine, keto isoleucine and keto leucine.

Combination, Acidification and Steam Distillation

In the present case, the sodium salt solutions of keto leucine (331 g of 6.9% w/w solution, containing 22.8 g of sodium salt), keto isoleucine (61 g of 18.8% w/w solution, containing 11.4 g of sodium salt) and keto valine (144 g of 8.6% w/w solution, containing 12.4 g of sodium salt) were charged in the concentrations specified in table 1 to give a ratio on active basis of 2:1:1.2 to an acid resistant vessel. The keto valine amount described in this example applies to the use of fresh liquors for salification (see examples 5-7 for description). When recycled mother liquors are used, the portion of keto valine can be reduced to 1. At ambient temperature and with stirring, 165 g 50% w/w sulphuric were charged to adjust the pH of the solution to pH<1. After pH adjustment, heat and vacuum were applied to achieve distillation at 60-80° C./200-300 mbar. Further water was added and distilled at 80° C. maximum under 270-300 mbar vacuum until approximately 42 g/g keto acid has been distilled. The distillate contained 2.2 weight % of BCKA.

Salification and Isolation

To a solution of 7.7 g (~0.5 molar equivalent) calcium acetate in 23.3 g water (~25% solution), was charged 550 g of free keto acid distillate containing approximately 12 g of branched chain keto acids. After checking the pH, a further amount of 25% calcium acetate solution was added to achieve a pH of 3-4. Once the pH was adjusted, the batch was heated to 75-80° C. distilled under 250-350 mbar vacuum to concentrate as described in the next steps.

First Batch with Fresh Liquors

The batch was concentrated to 15% w/w at 75-80° C., then cooled to 20-25° C. to crystallize. After stirring at 20-25° C. for 1 hour, the product was isolated by filtration and dried. The product yield was 11.8 g, corresponding to 78% (referring to the starting material). The mother liquors were retained for use in the next batches.

Follow on Batches with Recycled Mother Liquors

To 78 g of mother liquors, 15 g (0.5 molar equivalent) of calcium acetate were charged. To the calcium acetate/mother liquor solution, 550 g of free keto acid distillate containing approximately 12 g of branched chain keto acids in a ratio 2:1:1 keto leucine:keto isoleucine:keto valine was charged. Expected pH was 3-4. The batch was concentrated to ~11-13% w/w at 75-80° C., then cooled to ~20-25° C. to crystallize. After stirring at ~20-25° C. for 1 hour, the product was isolated by filtration and dried. The product yields were 12.2-14 g, corresponding to 80-94%. The mother liquors were retained for use in the next batches.

The product prepared by co-crystallization, on the other hand, is homogeneous as shown in FIG. 6, and has a more uniform particle size distribution (as shown in FIG. 7), making it suitable for applications without further treatment. FIG. 6 shows a microscope picture of co-crystallized branched chain keto acid calcium salts (2:1:1 keto leucine: keto isoleucine:keto valine) (magnitude: 100x, scale bar is 200 µm). FIG. 7 shows the particle size distribution (PSD) of co-crystallized branched chain keto acid calcium salt (2:1:1 keto leucine:keto isoleucine:keto valine)—x axis showing particle size in µm and y axis showing % of particles. Red line depicts sum of particles.

The effect of uniform particle size distribution can be further visualized when comparing the particle size distribution of the mixture of BCKAs co-crystallized according to the present invention with a mixture of BCKAs without any co-crystallization or co-processing.

As shown in FIG. 8 *a*), a uniform particle size distribution can be measured for co-crystallized branched chain keto acid salts. However, when the same branched chain keto acid salts are mixed without any co-crystallization or co-processing, three distinct peaks for the three keto acids can be detected, with keto isoleucine having much bigger particles than keto leucine and keto valine showing the smallest particle size, as depicted in FIG. 8 *b*). FIG. 8 shows particle size distribution (PSD) of a) co-crystallized branched chain keto acid calcium salts (2:1:1 keto leucine:keto isoleucine: keto valine) and b) mixture of branched chain keto acid calcium salts (2:1:1 keto leucine:keto isoleucine:keto valine), x axis showing particle size in µm and y axis showing volume % of particles.

Example 6: Preparation of Mixture of Calcium Salts (with Calcium Carbonate)

The branched chain keto acids are charged to BCKA mother liquors (ca. 5% w/v) in the following molar ratio: keto valine:keto leucine:keto isoleucine 1.1:2:1. The mixture is heated to 60° C., then portion-wise, 0.5 molar eq. of calcium carbonate is charged. The suspension is heated to >75° C. and after stirring for a period, the reaction mixture is cooled to ambient temperature. The solids are isolated by filtration, washed with water and dried.

Example 7: Preparation of Mixture of Calcium Salts (with Calcium Hydroxide)

A 5-10% solution (may be single or biphasic) comprising 2 eq. of the keto acid mixture composed of keto valine:keto leucine:keto isoleucine 1.1:2:1 in water (alternatively, mother liquors) is prepared, and heated to 50-70° C. At this temperature, 1 eq. of calcium hydroxide is charged. Once the addition is complete, the contents are heated to 75-90° C. to dissolve the solids, then the solution is cooled to ambient temperature. The resulting solids are isolated by filtration and washed with water. The solids may be dried at up to 60° C. under vacuum. The yield achieved was 40-80%. Higher yield was achieved when using recycled mother liquors.

Example 8: Preparation of Mixture of Calcium Salts

The following calcium salts were prepared using methods analogous to those described in Example 2 (to form the free acid) and Examples 4 to 7 for salification/isolation:

Keto phenylalanine/α-hydroxymethionine

Keto phenylalanine/keto valine

α-Hydroxymethionine/keto isoleucine

Example 9: Preparation of Mixture of Magnesium Salts (with Magnesium Acetate)

To a 5-10% solution of 1 eq. of magnesium acetate tetrahydrate in water is added a 30-60% methylisobutylketone (MIBK) solution of a keto acid mixture composed of keto valine:keto leucine:keto isoleucine 1.1:2:1 (BCKA) at 50-75° C. The biphasic solution is heated to 75-85° C., at which temperature phase separation is performed. The aqueous solution is concentrated under vacuum to minimum volume at 80° C. max, then, after addition of n-butanol, concentrated again to remove the n-butanol residual water (by azeotropic distillation) to afford a solid. The solids may be dried at up to 70° C. under vacuum. The yield achieved was 80-90%. The characteristics of the different magnesium salts of branched chain keto acids are shown in table 4.

TABLE 4

Overview over magnesium salts of branched chain keto acids: single keto acid salts and mixture of branched chain keto acid salts (2:1:1 keto leucine:keto isoleucine:keto valine)

|  | Keto leucine | Keto isoleucine | Keto valine | BCKA |
|---|---|---|---|---|
| Mw (anh.) | 282.4 | 282.4 | 254.3 | 275.4 (Ave.) |
| Formula | $C_{12}H_{18}O_6Mg$ | $C_{12}H_{18}O_6Mg$ | $C_{10}H_{14}O_6Mg$ |  |
| Structure | 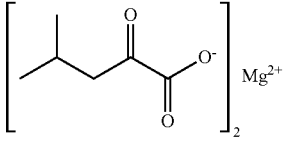 Keto Leu × 2 Mg | 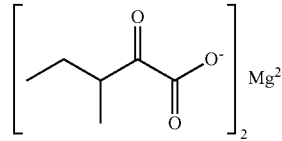 Keto ILe × 2 Mg | 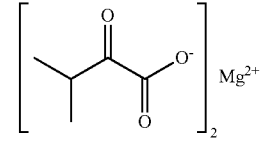 Keto Val × 2 Mg |  |
| Appearance | White powder | White powder | White powder | White solid |
| Mg Content, % (Theory, %) | 9.0 (8.5) | 8.35 (8.5) | 9.34 (9.45) | 10.0 (8.7) |
| HPLC/NMR Identity | Confirmed | Confirmed | Confirmed | Confirmed |

Following mixtures were also prepared:
mixed magnesium salts of keto leucine and keto isoleucine,
mixed magnesium salts of keto leucine and keto valine, and
mixed magnesium salts of keto isoleucine and keto valine.

Example 10: Preparation of Mixture of Magnesium Salts (with Magnesium Hydroxide)

A 5-10% solution (may be single or biphasic) comprising of 2 eq. of the keto acid in water (alternatively, mother liquors) is prepared, and heated to 50-70° C. At this temperature, 1 eq. of magnesium hydroxide is charged. Once the addition is complete, the contents are concentrated under vacuum at 75° C. until a solid is obtained. The solid is dried. The yield achieved was >90%.

Example 11: Preparation of Mixture of Mixed Calcium/Magnesium Salts at Different Ratios A 5-10% solution (may be single or biphasic) comprising 2 eq. of the keto acid in water (alternatively, mother liquors) is prepared, and heated to 50-70° C. At this temperature, total 1 eq. of magnesium/calcium hydroxide are charged in 2:1, 1:1 or 1:2 ratio. Once the addition is complete, the contents are concentrated under vacuum at 75° C. until a solid is obtained. The solid is dried. The yield achieved was >90%. The characteristics of the mixed calcium/magnesium salts of branched chain keto acids with different mixture ratios are shown in table 5.

TABLE 5

Overview over mixed calcium/magnesium salts of branched chain keto acids with different mixture ratios

|  | 2:1 Ca/Mg Salt | 1:1 Ca/Mg Salt | 1:2 Ca/Mg Salt |
|---|---|---|---|
| Mw (Average, anh.) | 286 | 283 | 280 |
| Formula | $C_{11.5}H_{17}O_{6.1}/3Mg.2/3Ca$ | $C_{11.5}H_{17}O_{6.1}/2Mg.1/2Ca$ | $C_{11.5}H_{17}O_{6.2}/3Mg.1/3Ca$ |
| Appearance | White solid | White solid | White solid |
| Ca Content, % (Theory, %) | 9.2 (9.6) | 7.1 (7.2) | 4.5 (4.8) |
| Mg Content, % (Theory, %) | 2.9 (2.9) | 4.5 (4.4) | 6.3 (5.8) |
| NMR Identity | Confirmed | Confirmed | Confirmed |

The invention claimed is:

1. A process for producing a homogenous mixture of two or more branched-chain keto amino acids, the process comprising:
   mixing two or more free branched-chain keto amino acids to produce mixed branched-chain keto amino acids; and
   co-crystallizing the mixed branched-chain keto amino acids with one or more alkaline earth metal salts.

2. The process of claim 1, wherein the alkaline earth metal of the alkaline earth metal salt is at least one selected from the group consisting of magnesium and calcium.

3. The process of claim 1, wherein the alkaline earth metal salt is at least one selected from the group consisting of calcium carbonate, calcium hydroxide, calcium acetate, calcium chloride, calcium oxide, magnesium hydroxide, and magnesium acetate.

4. The process of claim 1, wherein the two or more branched-chain keto amino acids comprise keto leucine, keto valine, and keto isoleucine.

5. The process of claim 1, wherein the two or more free branched-chain keto amino acids are charged in a desired molar ratio to water or a mother liquor solution, into which a stoichiometric amount of the alkaline earth metal salt has been charged.

6. The process of claim 1, wherein the two or more free branched-chain keto amino acids are added as an aqueous solution or as a solution in an organic solvent.

7. The process of claim 1, wherein the mixed branched-chain keto amino acids are purified before the co-crystallizing, using at least one purification technique selected from the group consisting of steam distillation, solvent extraction, ion exchange chromatography, and crude crystallization with an alkaline earth metal salt.

8. The process of claim 7, wherein the mixed branched-chain keto amino acids are purified before the co-crystallizing, using combined steam distillation or solvent extraction.

9. A mixture of at least two branched-chain keto amino acids obtained by the process of claim 1, wherein the mixture contains mixed alkaline earth metal salts and has a uniform particle size distribution and a homogenous crystal form.

10. The mixture of claim 9, wherein the size of the particles is not larger than 400 μm.

11. The mixture of claim 9, which comprises mixed calcium or magnesium salts of keto leucine and keto isoleucine.

12. The mixture of claim 9, which comprises mixed calcium or magnesium salts of keto leucine and keto valine.

13. The mixture of claim 9, which comprises mixed calcium or magnesium salts of keto isoleucine and keto valine.

14. The mixture of claim 9, which comprises mixed calcium or magnesium salts of keto leucine, keto isoleucine, and keto valine in an approximate molar ratio of 2:1:1.

15. The mixture of claim 9, which comprises mixed calcium or magnesium salts of keto leucine, keto isoleucine, and keto valine.

16. A foodstuff, a food supplement, or a pharmaceutical product comprising the mixture of claim 9.

17. A method of preparing a foodstuff, a food supplement, or a pharmaceutical product, comprising:

adding the mixture of claim 9 to a product.

* * * * *